United States Patent [19]

Rule et al.

[11] Patent Number: 4,806,698
[45] Date of Patent: Feb. 21, 1989

[54] LIQUID PHASE ISOMERIZATION OF IODOAROMATIC COMPOUNDS

[75] Inventors: Mark Rule; Gerald C. Tustin, both of Kingsport, Tenn.

[73] Assignee: Eastman Kodak Company, Rochester, N.Y.

[21] Appl. No.: 29,956

[22] Filed: Mar. 25, 1987

[51] Int. Cl.$^4$ .................... C07C 17/12; C07C 25/00
[52] U.S. Cl. ................................ 570/202; 570/203; 570/208
[58] Field of Search .................... 570/202, 203, 208

[56] References Cited

U.S. PATENT DOCUMENTS

| | | | |
|---|---|---|---|
| 3,214,482 | 10/1965 | Caropreso et al. | 570/202 |
| 3,363,010 | 1/1968 | Schwarzenbek | 570/203 |
| 4,368,339 | 1/1983 | Tada et al. | 570/202 |

FOREIGN PATENT DOCUMENTS

| | | | |
|---|---|---|---|
| 0046665 | 3/1982 | European Pat. Off. | 570/202 |
| 0062261 | 10/1982 | European Pat. Off. | 570/202 |
| 0181790 | 5/1986 | European Pat. Off. | 570/203 |
| 0183579 | 6/1986 | European Pat. Off. | 570/203 |
| 0077631 | 5/1982 | Japan | 570/203 |
| 0144330 | 8/1983 | Japan | 570/202 |

OTHER PUBLICATIONS

Advanced Organic Chemistry: Reactions, Mechanisms, and Structure Mar., McGraw-Hill, 1968, p. 405.
J. Org. Chem. vol. 35, No. 10, 1970, Baird et al., Halogenation with Copper (II) Halides. The Synthesis of Aryl Iodides.
Institute of Catalysis, Siberian Branch of the Academy of Sciences of the USSR, vol. 23, No. 4, pp. 992–994, Jul.-Aug., 1982; Gorodetskaya et al., Oxidative Bromination of Aromatic Compounds.... Chemical Economy & Engineering Review, Apr. 1984, vol. 16, No. 4 (No. 177) Itatani: International Technological Trends in $C_1$ Chemistry.

Primary Examiner—Werren B. Lone
Attorney, Agent, or Firm—Charles R. Martin; W. P. Heath, Jr.

[57] ABSTRACT

The invention relates to a process for isomerizing liquid iodoaromatic compounds over an acid catalyst.

13 Claims, No Drawings

LIQUID PHASE ISOMERIZATION OF IODOAROMATIC COMPOUNDS

BACKGROUND OF THE INVENTION

1. Field of the Invention

The present invention relates to processes for transiodinating aromatic compounds wherein undesired isomers are contacted with an acidic catalyst in the liquid phase to effect isomerization or transiodination.

2. Discussion of Background

It has long been desired to be able to derivatize aromatic compounds and in particular condensed ring aromatic compounds in commercially attractive guantities since many of these compounds possess properties which would fill long sought needs. In particular. the compound 2,6-naphthalene dicarboxylic acid or its esters is particularly desired for use in the manufacture of polyesters which would have excellent barrier properties when fabricated into films. bottles or coatings. However, known techniques for producing 2,6-naphthalene dicarboxylic acid and esters are very expensive and impractical for commercial exploitation.

DESCRIPTION OF THE PRIOR ART

Synthesis of iodobenzene starting from benzene and iodine is usually carried out in the liguid phase in the presence of an oxidative agent. preferably nitric acid. Such techniques have been described in the literature and in particular in Japanese 58/77830, U.S.S.R. patent 453392 and by Datta and Chatterjee in the *Journal of the American Chemical Society*, 39, 437, (1917). Other oxidative agents have also been suggested but none of these have proven to be more efficient or convenient than nitric acid. Typical of the other oxidative agents which have been suggested are iodic acid. sulfur trioxide and hydrogen peroxide as described by Butler in the *Journal of Chemical Education*, 48, 508, (1971). The use of metal halogenides to catalyze iodination has been suggested by Uemura, Noe, and Okano in the *Bulletin of Chemical Society of Japan*, 47, 147, (1974). The concept of direct iodination of benzene in the gas phase over the zeolite 13X has been suggested in Japanese patent publication 82/77631 in the absence of any oxidizing agent.

Ishida and Chono in Japanese Kokai 59/219241 have suggested a technique for oxyiodinating benzene over very acidic zeolite catalyst having a silica to alumina ($SiO_2:Al_2O_3$) ratio of greater than 10. In this technique benzene is reacted ith iodine in the presence of oxygen to produce iodinated benzene.

Paparatto and Saetti disclosed in European Patent Applications 181,790 and 183,579 technigues or oxyiodination of benzene over zeolite catalysts. European Patent Application 181,790 suggests the use of ZSM-5 and ZSM-11 type zeolites which have been exchanged prior to use with the least one bivalent or triva,lent cation. According to this disclosure the utilization of these zeolites in the acid or alkaline form results in a rapid decrease in catalytic activity in relatively few hours.

European patent Application 183,579 suggests the utilization of X type or Y type of zeolite in nonacid form. According to 183,579 the X or Y zeolites have to be used in the form exchanged with monovalent, bivalent or trivalent cations and in particular with alkaline or rare earth cations. The techniques of European patent application 181,790 and 183,579 prepare the monoiodobenzene in selectivities in excess of 90% and only distinctly minor amounts of the diiodobenzene compounds.

RELATED APPLICATIONS

Copending application Ser. No. 912,806 filed Sept. 29, 1986, Ser. No. 029,959 filed Mar. 25, 1987, Ser. No. 029,898, filed Mar. 25, 1987 and Ser. No. 029,899 filed Mar. 25, 1987 disclose techniques for iodinating aromatic compounds over non-acid catalysts. The disclosure of these applications is herein incorporated by reference. All of these techniques produce more than one iodinated aromatic product. Economic constraints reguire the recovery of iodine values in the undesired isomers. It would therefore be advantageous to discover a process whereby undesired iodoaromatic isoeers can be conVerted into desired isomers.

Ser. No. 029,899 filed Mar. 25, 1987, discloses a process of isomerizing or transiodinating iodoaromatic compounds in the presence of a non-acid catalyst. This process regires the vaporization of the iodoaromatic compound and therefore reguires a substantial input of energy Consequently. this process works well only with relatively volatile iodoaromatic compounds. polynuclear iodoaromatic compounds freguently have high boiling points and are difficult to vaporize without concomittent decomposition. Vaporization of these compounds reguires a substantial input of heat energy.

There is presently no effective means of converting undesired isomers produced in these processes into specifically desired isomers at lower temperatures and without the deoomposition of the iodoaromatic compounds.

Accordingly, a need exists for a process by which undesired iodoaromatic isomers can be easily and economically isomerized to desired isomeric products.

A further need exists for a process by which undesired iodoaromatic isomers can be isomerized at relatively low temperatures and in a liguid phase without decomposition of the isomers.

BRIEF DESCRIPTION OF THE INVENTION

Accordingly, one object of the present invention comprises a technigue for isomerizing an iodoaromatic compound over an acidic catalyst to effect isomerization to desired isomers.

A further object of the present invention comprises a technigue for the liguid phase isomerization of an iodoaromatic compound at relatively low temperatures over an acidic catalyst to effect transiodination to desired isomers.

These objects and further objects of the present invention which will become apparent from the following disclosure have been attained by the process of the present invention which comprises reacting iodoaromatic compounds over an acidic catalyst to effect isomerization and/or transiodination.

DESCRIPTION OF THE PREFERRED EMBODIMENTS

The term "isomerization" as used herein means intra- or intermolecular iodine transfer.

The active catalysts utilized in the present technigue are generally characterized as being solid acids. Some acidic zeolites have outstanding catalytic activity. Non-zeolitic solid acids are also useful for this invention. The acid sites may be of the Lewis type or Bronsted type. The Bronsted acid sites result from the hydroxyl groups present in the catalyst while Lewis acid sites are generally thought to result from cationic coordinative unsaturation.

Acidity is generally introduced into zeolites by the decomposition of the ammonium ion-exchanged form, by hydrogen-ion exchange, or by dehydration of zeolites containing multi-valent cations. Preferred acidic zeolite catalysts include acidic Y-type zeolites, such as H-Y and rare earth-H-Y zeolites; acidic X-type zeolites. such as rare earth-H-X zeolites, and acidic L-type zeolites, such as H-L zeolites. Preferred non-zeolitic catalysts having acid sites include the acidic silica-alumina catalysts, such as Davidson 980-13.

Surprisingly, catalysts widely regarded as having very high acidity, such as H-ZSM-5 and H-mordenites possess much lower levels of activity than the catalysts noted above. Additionally, catalyst such Na-X and K-X. which possess activity in the vapor phase at temperatures of about 325° C. are inactive in the liquid phase below temperatures of about 250° C.

The aromatic compounds which can be utilized in the practice of the present invention are essentially any aromatic compound including substituted and unsubstituted aromatics. Suitable aromatic compounds include hydrocarbon aromatics oxygen containing aromatics and sulfur containing aromatics. Typical hydrocarbon aromatics include benzene and biphenyl, condensed ring aromatics such as naphthalene and anthracene, sulfur containing aromatics including thiophene and benzothiophene, oxygen containing aromatics such as furan and benzofuran, and substituted aromatics such as sulfones, diaryl ethers, diaryl carbonyls, diaryl sulfides and the like. Aromatic compounds substituted by alkyl groups are generally not preferred for utilization in the present technigue. It has been found that with alkyl substituted aromatics the iodination reaction is not limited to the aromatic ring but that one obtains a mixture of products. That is, the products are iodinated not only on the ring but also on the side chains. Thus, while alkyl substituted aromatics can be utilized in the present technigue their use is not preferred.

Whether the catalyst is an acidic zeolite or an acidic non-zeolite material a given feed yields approximately the same thermodynamic distribution of products. Therefore, the product distribution obtained is not critically dependent on the choice of catalyst and depends mainly on the molar ratio of aromatic to iodide. The rate of reaction, however, is dependent on catalyst activity and reaction temperature. For iodobenzenes or iodonaphthalenes, the preferred temperatures are between about 100° C. and about 275° C. Similar temperature ranges would be used for other iodinated aromatic compounds. More preferred reaction temperatures are between about 180° C. and 250° C. The use of higher or lower temperatures is a matter of choice depending on the nature of the catalyst and iodoaromatic compounds to be isomerized. The upper limit of the temperature range is practically determined by the temperature at which decomposition of the iodoaromatic compound begins to occur. The use of relatively lower temperatures is preferred since the decomposition of the iodoaromatic compounds is minimized.

The isomerization reaction is preferably run in the absence of solvent. However, the reaction will proceed egually well in the presence of suitable organic solvents which are not susceptible to iodination under the conditions employed in the isomerization reaction. Suitable solvents can be selected from the alkanes and cycloalkanes, such as hexane, heptane, octane, nonane, cyclohexane, decalin, etc.

The pressure at which the process is conducted is not critical and can range from subatmospheric to superatmospheric. The utilization of elevated pressures may be useful when the process is operated in the presence of solvent. particularly solvents with relatively low boilin points. The use of higher pressures allows the isomerization reaction to be run at elevated temperatures, i.e., temperatures above the boiling point of the solvent. In general, pressures from atmospheric to about 600 psig have proven satisfactory although higher or lower pressures can be utilized. Alternatively, the isomerization reaction can be conducted as a vapor-phase process, if desired.

The isomerization reaction is preferably carried out in the absence of oxygen, although the absence of oxygen is not essential and the isomerization reaction will occur even though oxygen is present in the system either as pure oxygen, a mixture of oxygen and inert gases or air.

The isomerization of iodoaromatic compounds in this fashion is quite surprising and unexpected, since the isomerization of haloaromatic compounds is considered to be a difficult process. reguiring a strongly acidic catalyst and long reaction times. For example, see Olah, *Journal of Organic Chemistry*, 27, 3469 (1962).

While not being bound to any particular theory, it is believed that the ready isomerization of iodoaromatic compounds is due to the fact that reaction (I) is unigue among the aromatic halogenation reactions in having a positive free energy of reaction. The equilibrium in this reaction lies strongly to the left.

$$ArH + I_2 \rightleftharpoons ArI + HI \qquad (I)$$

In the iodoisomerization reaction the analogous reaction (II) occurs:

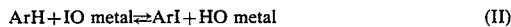

$$ArH + IO\text{ metal} \rightleftharpoons ArI + HO\text{ metal} \qquad (II)$$

Thus in order to accomplish the isomerization, it is necessary only to operate under conditions where some sufficiently acidic catalyst is present. This will effect deiodination according to the reverse of reaction (II) since it is an eguilibrium reaction. The iodo species thus formed is available for reaction and the net effect is a redistribution of iodide among the aromatic species present. In the presence of uniodinated species, the net effect is to decrease the concentration of di- and triiodinated compounds and increase the concentration of mono-iodinated species.

The isomerization reaction can be operated as a continuous process or can be carried out as batch or semi-batch processes if desired and can be coupled to any suitable iodination reaction. A preferred embodiment is to couple the isomerization reaction to an oxyiodination reaction, as described in application Ser. No. 912,806. When the oxyiodination reaction is performed as a continuous process, the isomerization reaction can be performed continuously by accepting the reaction product from the oxyiodination reaction. One or more desired products may be isolated prior to and/or after the isomerization reaction. The remaining effluents from the isomerization reaction can then be recycled and again passed through the isomerization or oxyiodination process. It is also possible to pass the effluent from the oxyiodination reaction through several isomerization catalysts beds isolating one or more desired products after each isomerization reaction.

A particular preferred embodiment is to transiodinate more highly iodinated coproducts with the uniodinated aromatic feed to produce a monoiodoaromatic product, which may then be fed to an (oxy)iodination process, if desired. When operated in this embodiment, there is very little loss of reactant materials and the products can be recycled continuously to produce any one of a number of desired isomers. Preferably, monoiodinated and diiodinated products are produced. The isomerization reaction works egually well for single ring iodoaromatics and polyaromatic iodo compounds. preferred reactants for the isomerization reaction are iodobenzenes iodobiphenyls and iodonaphthalenes.

Another embodiment of this invention is to iodinate an aromatic species by transferring iodide from another species, such as iodinating naphthalene by transferring iodide from iodobenzene. Obviously, it is possible to combine various aspects of these different embodiments to achieve the desired products and economic efficiency.

If the isomerization catalyst reguires regeneration due to the deposition of carbon on the catalyst the catalyst can be easily reactivated by passing air or oxygen over the catalyst for several hours at elevated temperatures.

The following examples are presented to illustrate the present invention but are not intended in any way to limit the scope of the invention which is defined by the appended claims. Obvlously numerous modifications and variations of the present invention are possible in light of the above teachings, and that the invention may be practiced otherwise than as specifically described herein.

In the examples below. the stated amounts of reactants and catalyst were mixed in a reaction tube fitted with a ground glass joint and stopper and placed in a heat block at the desired temperature. Samples were removed periodically for analysis by GC. Analysis reported are mole %.

EXAMPLE 1

1.0 grams SK-500 (rare earth—H-Y)
5.0 grams 1-iodonaphthalene
200 deg. C

After 20 minutes the product analyzed as 14.5% naphthalene 26.9% 2-iodonaphthalene, 43.2% 1-iodonaphthalene, and 15.2% diiodonaphthalenes (mixture of isomers). After 60 minutes the product analyzed as 23.2% naphthalene, 35.1% 2-iodonaphthalene 19.9% 1-iodonaphthalene, 20.8% diiodonaphthalenes and 1.0% triiodonaphthalenes.

EXAMPLE 2

1.0 grams LZY-72 (H-Y zeolite)
2.0 grams monoiodonaphthalenes (78% 2-iodo; 22% 1-iodo)
200 deg C After 50 minutes, the product analyzed as 14.3% naphthalene, 34.5% 2-iodonaphthalene, 30.4% 1-iodonaphthalene, and 20.4% diiodonaphthenes (mixture of isomers, the 2,6 isomer constituting 20.3% of the diiodonaphthalenes).

EXAMPLE 3

0.2 grams H-L (prepared from EZL-1 by NH$_4$Cl exchanged with calcination)
0.5 grams monoiodonaphthalenes (78% 2-iodo; 22% 1-iodo)
230 deg C After 75 minutes, the product analyzed as 14.8% naphthalene, 40.1% 2-iodonaphthalene, 21.7% 1-iodonaphthalene, and 23.4% dIiodonaphthalenes (mixture of isomers; 2,6-diiodonaphthalene comprised 13.4% of the diiodonaphthalenes).

EXAMPLE 4

2.0 grams Davidson GR 980-13 (13% Al$_2$O$_3$-87% SiO$_2$)
5.0 grams 1-iodonaphthalene
200 deg C After 50 minutes the product analyzed as 7.1% naphthalene, 14.3% 2-iodonaphthalene, 71.5% 1-iodonaphthalene, and 6.9% diiodonaphthalenes.

EXAMPLE 5

0.2 grams H-ZSM-5
0.5 grams monoiodonaphthalenes (78% 2-iodo; 22% 1-iodo)
200 deg C After 5 hours, the product analysed as 2.9% naphthalene, 74% 2-iodonaphthalene, 21% 1-iodonaphthalene, and 2% diiodonaphthalenes. This example shows that, although possessing some activity, the ZSM-5 type catalyst has much lower activity than the Y-type catalysts.

EXAMPLE 6

0.2 grams rare earth-H-X
0.5 grams monoiodonaphthalenes (same as Example 5)
200 deg C The rare earth-H-X was prepared by exchanging Na-X three times with rare earth nitrates. then once with ammonium chloride followed by calcination. The product after two hours consisted of 19.4% naphthalene, 37.4% 2-iodonaphthalene, 20.7% 1-iodonaphthalene, and 22.5% diiodonaphthalenes, 20.3% of which is the 2,6 isomer.

EXAMPLE 7

1.0 grams SK-500
1.25 grams naphthalene
3.75 grams diiodonaphthalene (70% 2.6; 30% 2.7 isomer)
200 deg C After 60 minutes the product distribution was essentially identical to that of Example 1. This demonstrates that the isomerization reaction proceeds equally well in both directions.

EXAMPLE 8

1.0 grams SK-500
1.25 grams naphthalene
3.25 grams p-diiodobenzene
200 deg C

After 70 minutes, the product consisted of 11.7% iodobenzene, 26.3% naphthalene, 6.2% diiodobenzenes, 26.2% 2-iodonaphthalene, 15.3% 1-iodonaphthalene, and 14.2% diiodonaphthalenes. This demonstrates the transfer of iodine from one aromatic species to another. The benzene coproduct was lost through evaporation.

EXAMPLE 9

1.0 grams K-X 5.0 grams monoiodonaphthalenes (same as in Example 5)
200 deg C

After five hours, less than 0.2% naphthalene was observed in the reaction mixture, indicating that the K-X material is catalytically inactive under these conditions.

EXAMPLE 10

0.2 grams Zeolon-H (acidic mordenite)
0.5 grams monoiodonaphthalenes (same as in Example 5)
230 deg C After 75 minutes the reaction product contained 3.1% naphthalene, 67.2% 2-iodonaphthalene, 18.8% 1-iodonaphthalene, and 3.2% diiodonaphthalenes. This example shows that this acidic zeolite, like the H-ZSM-5 catalyst, possesses lower activity than the preferred catalysts.

EXAMPLE 11

5.0 grams iodobenzene
1.0 grams SK-500
180 deg C

After two hours, the reaction product contained 66.3% iodobenzene, 31.4% diiodobenzenes, and 2.3% triiodobenzenes. The benzene reaction coproduct was lost through evaporation.

EXAMPLE 12

1.0 grams SK-500
5.0 grams 1-iodonaphthalene
150 deg C

After two hours, the reaction product analyzed as 9.3% naphthalene, 58.2% 1-iodonaphthalene, 23.1% 2-iodonaphthalene, and 9.4% diiodonaphthalenes.

While the invention has been described in detail with particular reference to preferred embodiments thereof, it will be understood that variations and modifications can be effected within the spirit and scope of the invention.

We claim:

1. A process of isomerizing a liquid mono-, di- or triiodoaromatic compound selected from the group consisting of benzene, biphenyl, naphthalene, anthracene, thiophene, benzothiophene, furan and benzofuran comprising contacting said liquid iodoaromatic compound with an acidic zeolite or silica-alumina solid catalyst, wherein the iodine present in said iodoaromatic compound is redistributed among the molecules of said iodoaromatic compound to form an isomerized product.

2. The process of claim 1, wherein said acidic catalyst is a zeolite.

3. The process of claim 2, wherein said zeolite is an acidic Y-type zeolite, acidic X-type zeolite or an acidic L-type zeolite.

4. The process of claim 1, wherein said acidic catalyst is an acidic silica-alumina catalyst.

5. The process of claim 1, wherein said iodoaromatic compound is an iodobenzene, an iodobiphenyl or an iodonaphthalene.

6. The process of claim 1, wherein said contacting step in conducted in the presence of an inert solvent.

7. The process of claim 1, wherein said contacting step occurs at temperatures between about 100° C. and 275° C.

8. The process of claim 7, wherein said contacting step occurs at temperatures between about 180° C. and 250° C.

9. The process of claim 1, wherein said iodoaromatic compound is a product resulting from an oxyiodination reaction.

10. The process of claim 9, wherein said contacting step is performed continuously and at least a portion of the product of said contacting step is recycled to the beginning of said contacting step.

11. A process for iodinating an aromatic compound comprising
    (a) reacting iodine and an aromatic compound selected from the group consisting of benzene, biphenyl, naphthalene, anthracene, thiophene, benzothiophene, furan and benzofuran in the presence of oxygen over a non-acidic catalyst to produce a mono-, di- or triiodoaromatic compound; and
    (b) contacting the iodoaromatic compound while in a liquid phase with an acidic zeolite or silica-alumina catalyst, wherein the iodine present in said iodoaromatic compound is redistributed among the molecules of said iodoaromatic compound to form an iosomerized product.

12. The process of claim 11, wherein said aromatic compound is benzene, naphthalene or biphenyl.

13. The process of claim 11, wherein said acidic catalyst is a zeolite.

* * * * *